(12) United States Patent
Bond et al.

(10) Patent No.: US 9,880,096 B2
(45) Date of Patent: Jan. 30, 2018

(54) RESONANT OPTICAL TRANSDUCERS FOR IN-SITU GAS DETECTION

(71) Applicant: Lawrence Livermore National Security, LLC, Livermore, CA (US)

(72) Inventors: Tiziana C Bond, Livermore, CA (US); Garrett Cole, Vienna (AT); Lynford Goddard, Champaign, IL (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 245 days.

(21) Appl. No.: 14/884,716

(22) Filed: Oct. 15, 2015

(65) Prior Publication Data
US 2016/0033397 A1 Feb. 4, 2016

Related U.S. Application Data

(63) Continuation of application No. 13/674,839, filed on Nov. 12, 2012, now Pat. No. 9,377,399, which is a
(Continued)

(51) Int. Cl.
*G01N 21/39* (2006.01)
*H01S 5/10* (2006.01)
(Continued)

(52) U.S. Cl.
CPC ......... *G01N 21/39* (2013.01); *H01S 3/08059* (2013.01); *H01S 3/1053* (2013.01); *H01S 3/1055* (2013.01); *H01S 5/10* (2013.01); *G01N 21/774* (2013.01); *G01N 2021/396* (2013.01); *G01N 2021/399* (2013.01); *G01N 2201/068* (2013.01); *G01N 2201/06113* (2013.01); *H01S 5/0028* (2013.01); *H01S 5/18366* (2013.01);
(Continued)

(58) Field of Classification Search
None
See application file for complete search history.

(56) References Cited

U.S. PATENT DOCUMENTS 6,785,432 B2    8/2004  Letant et al.
2002/0068018 A1  6/2002  Pepper et al.
(Continued)

OTHER PUBLICATIONS

Armani et al., "Heavy water detection using ultra-high-Q microcavities", Opt. Lett., v. 31, No. 12, pp. 1896-1898, 2006.
(Continued)

*Primary Examiner* — Yara B Green
(74) *Attorney, Agent, or Firm* — John P. Wooldridge

(57) ABSTRACT

Configurations for in-situ gas detection are provided, and include miniaturized photonic devices, low-optical-loss, guided-wave structures and state-selective adsorption coatings. High quality factor semiconductor resonators have been demonstrated in different configurations, such as micro-disks, micro-rings, micro-toroids, and photonic crystals with the properties of very narrow NIR transmission bands and sensitivity up to $10^{-9}$ (change in complex refractive index). The devices are therefore highly sensitive to changes in optical properties to the device parameters and can be tunable to the absorption of the chemical species of interest. Appropriate coatings applied to the device enhance state-specific molecular detection.

32 Claims, 10 Drawing Sheets

Related U.S. Application Data continuation-in-part of application No. 12/406,838, filed on Mar. 18, 2009, now Pat. No. 8,309,929.

(60) Provisional application No. 61/037,642, filed on Mar. 18, 2008, provisional application No. 61/037,645, filed on Mar. 18, 2008.

(51) Int. Cl.
  H01S 3/08 (2006.01)
  H01S 3/105 (2006.01)
  H01S 3/1055 (2006.01)
  G01N 21/77 (2006.01)
  H01S 5/183 (2006.01)
  H01S 5/00 (2006.01)

(52) U.S. Cl.
  CPC ....... H01S 5/18369 (2013.01); H01S 2302/00 (2013.01)

(56) References Cited

U.S. PATENT DOCUMENTS

| | | |
|---|---|---|
| 2006/0203870 A1 | 9/2006 | Kim |
| 2007/0133001 A1 | 6/2007 | Cox et al. |
| 2009/0212278 A1* | 8/2009 | Jorgenson ............. H01L 33/105 257/13 |
| 2010/0303468 A1* | 12/2010 | Mastro ................... B82Y 20/00 398/118 |

OTHER PUBLICATIONS

Armani et al., "Ultra-high-Q toroid microcavity on a chip", Nature Pub. Group, v. 421, pp. 925-928, 2003.
Barillaro et al., "Low-Concentration NO2 Detection With an Adsorption Porous Silicon FET", IEEE Sensors Journ., v. 6, No. 1, pp. 19-23, 2006.
Barrettino et al., "CMOS Monolithic Metal-Oxide Gas Sensor Microsystems", IEEE Sensor Journ., v. 6, No. 2, pp. 276-286, 2006.
Borselli et al., "Measuring the role of surface chemistry on silicon microphotonics", Appl. Phys. Lett., v. 88, pp. 131114-1-131114-3, 2006.
Cheng et al., "Pd-oxide Al0.24Ga0.76As (MOS) High Electron Mobility Transistor (HEMT)-Based Hydrogen Sensor", IEEE Sensor Journ., v. 6, No. 2 pp. 287-292, 2006.
Fetzer et al., "Midinfrared laser absorption spectroscopy in coiled hollow optical waveguides", Proc. SPIE, v. 4957, pp. 124-133, 2003.
Goddard et al., "Functionalized Lateral Surface Coated Lasers for Chem-Bio Detection," IEEE Sensors 2007, Conf., pp. 1181-1184, 2007.
Goddard et al., "Rapidly Reconfigurable All-Optical Universal Logic Gate" (invited), Proc. SPIE Optics, v. 6368, pp. 63630H-1-63680H-13, 2006.
Harper et al., "Detection of Nitric Oxide and Nitrogen Dioxide with Photoluminescence Porous Silicon", Anal. Chem., v. 68, pp. 3713-3717, 1996.
Kim et al., "Hydrogen Gas Sensor Using Pd Nanowires Electro-Deposited Into Anodized Alumina Template", IEEE Sensor Journ., v. 6, No. 3, pp. 509-513, 2006.
Kim et al., "Sensitivity enhancement for CO gas detection using a SnO2—CeO2—PdOx system", Sensors and Actuat., v. B 107, pp. 825-830, 2005.
Kozodoy et. al, "Small-Bore Hollow Waveguide Infrared Absorption Cells for Gas Sensing", Appl. Spec., v. 50, No. 3, pp. 415-417, 1996.
Krioukov et al."Sensor based on an integrated optical microcavity", Op. Lett, v. 27, No. 7, pp. 512-514, 2002.
Lowry, et al., "RadSensor: Xray Detection by Direct Modulation of an Optical Probe Beam", Proc. SPIE, v. 5194, pp. 193-204, 2004.
Mitsubayashi et al., "Bio-optical Gas-Sensor (Sniffer Device) with a Fiber Optic Oxygen Sensor", Conf. on Optoelec. and Microelec. Materials and Devices; COMMAD 2002 , IEEE, pp. 213-216, 2002.
Opilski, et al., "Determination of the optical parameters of thin palladium layers and their application in optical hydrogen sensors", Proc. of SPIE, v. 5576, pp. 208-212, 2004.
Ouyang et al., "Biosensing with One Dimensional Photonic Bandgap Structure", Proceedings SPIE v. 5511, p. 71-80, 2004.
Pipino et al., "Evanescent wave cavity ring-down spectroscopy with a total-internal-reflection minicavity", Rev. Sci. Instrum., v 68, No. 8, pp. 2978-1989, 1997.
Pocha et al., "Gain Lever Characterization in Monolithically Integrated Diode Lasers", Proc. of SPIE, v. 5722, pp. 288-298, 2005.
Pickrell et al., "Random-hole optical fiber evanescent-wave gas sensing", Opt. Lett., v. 29, No. 13, pp. 1476-1478, 2004.
Puscasu et al., "Extraordianry emission form 2-dimensional plasmonic-photonic crystals", Journ. Appl. Phys., v. 98 pp. 013531-1-013531-5, 2005.
Saito et al., "Spectroscopic gas sensing with infrared hollow waveguide", SPIE, v. 1796, pp. 231-242, 1992.
Savvate'ev et al., "Integrated organic light emitting device/fluorescence-based chemical sensor", Appl. Phys. Lett., v. 81, No. 81, pp. 4652-4654, 2002.
Stokes et al., "Surface-Enhanced-Raman-Scattering-Inducing Nanoprobe for Spectrochemical Analysis", Appl. Spect. v. 58, No. 3, p. 292-298, 2004.
Talley, "Intracellular pH Sensors Based on Surface-Enhanced-Raman Scattering", Anal. Chem, v. 76, pp. 7064-7068, 2004.
Villatoro et al., "Fast detection of H2 with nano fiber tapers coated with ultra thin palladium layers", Opt. Exp., v.13, No. 13, pp. 5087-5092, 2005.
Wang et al., "Nano-crystalline tungsten oxide NO2 sensor", Sensors and Actuators, v. B 94, pp. 343-351, 2003.
Welty et al., "Integrated laser with low-loss high index-contrast waveguides for OEICs", Proc. of SPIE, v. 5629, pp. 49-60, 2005.
Yan et al., "Surface-Enhanced Raman Scattering Detection of Chemical and Biological Agent Simulants", IEEE Sensors Journ., v. 5, No. 4, pp. 665-670, 2005.
Zhao et al., "All-optical Hydrogen sensor based on high alloy content palladium thin film", Sensors and Actuaturtors, v. B 113, pp. 532-538, 2006.

* cited by examiner

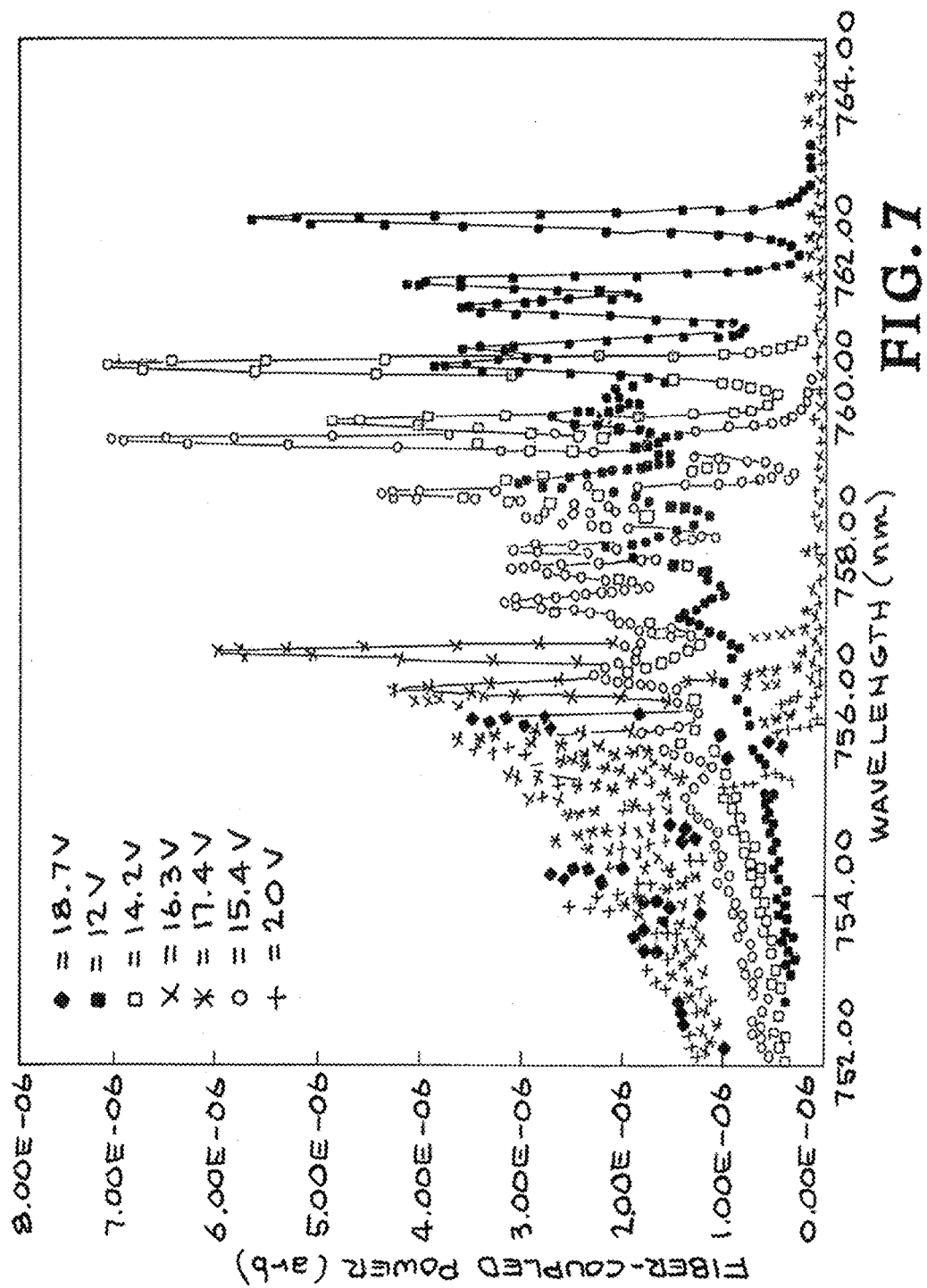

RESONANT OPTICAL TRANSDUCERS FOR IN-SITU GAS DETECTION

CROSS-REFERENCE TO RELATED APPLICATIONS

This application is a Continuation of U.S. patent application Ser. No. 13/674,839, titled "Resonant Optical Transducers for In-Situ Gas Detection," filed Nov. 12, 2012, incorporated herein by reference, which is a Continuation in Part of U.S. patent application Ser. No. 12/406,838, titled "Tunable Photonic Cavities for In-Situ Spectroscopic Trace Gas Detection," filed Mar. 18, 2009, incorporated herein by reference, which claims priority to U.S. Provisional No. 61/037,642, filed Mar. 18, 2008, titled: "Tunable Photonic Cavities for In-Situ Spectroscopic Trace Gas Detection," incorporated herein by reference and also claims priority to U.S. Provisional No. 61/037,645, titled: "Resonant Optical Transducers for In-Situ Gas Detection," filed Mar. 18, 2008, incorporated herein by reference.

STATEMENT REGARDING FEDERALLY SPONSORED RESEARCH OR DEVELOPMENT

The United States Government has rights in this invention pursuant to Contract No. DE-AC52-07NA27344 between the U.S. Department of Energy and Lawrence Livermore National Security, LLC, for the operation of Lawrence Livermore National Laboratory.

BACKGROUND OF THE INVENTION

Field of the Invention

The present invention relates to emission monitoring and control of gases in various environments, and more specifically, it relates devices for in-situ gas detection.

Description of Related Art

Emission monitoring and control of gases in various environments is critical in determining the overall health of a given system. In particular, low-weight molecule sensing (e.g., $H_2$, $O_2$, $CO_2$, $NO_2$, $C_2H_2$) will indicate possible inward/outward leaks (Ar, $O_2$, $H_2O$, He), identify degradation ($H_2O \rightarrow$ corrosion, $NO_x \leftarrow$ He), identify aging mechanisms and incompatibilities, detect contamination and reactions ($H_2$, $NO_x$) and detect outgassing ($CO_x$, $O_2$). Such system designs call for in-situ, minimally invasive, trace-gas analysis, with the requirement of parts per million (ppm) sensitivity, at a few atmospheres pressure of $N_2$ air and within a cubic centimeter volume. In general, such sensors can benefit with on-board, smart self-calibrating subsystems to augment the basic device.

Examples of systems that can benefit from trace-gas sensors include compact and highly multiplexed autonomous systems for laboratory or field monitoring of nuclear, chemical or biological threats, for combustion and environmental research, pollution monitoring, space exploration, aircraft cabin atmosphere monitoring, nuclear proliferation detection, stockpile stewardship, etc.

Presently, there exist a variety of sensors based on optical techniques, including optoelectronics and photonics, optical fiber sensors, as well as electrical and electromechanical technologies. Tables 1A and 1B tabulate prior art sensor techniques and properties as a function of selected device parameters. Tables 1C and 1D provide similar device characteristics, as applied to embodiments of the present invention. For each given sensor listed, entries in the table include its respective principles of operation, typical species to be sensed, performance, sensitivity, lifetime and other relevant device parameters, as well as representative archival references.

Referring to tables 1A and 1B, to further place the present invention within the context of state-of-the art sensors, are summarized relevant performance figures-of-merit in this survey of existing and promising technologies that have the potential to address typical applications issues, including the following: (1) low cross-sensitivity in the presence of other trace gases; (2) time-dependent concentration tracking; (3) limitations in terms of null outgassing; (4) stockpile stewardship; (5) relative compactness; (6) degree of maintenance; (7) moving parts, if required; (8) device weight; (9) power operation and (10) reliability and lifetime.

The prior art entries are partitioned in tables 1A and 1B, based on the underlying technology and principles of operation, including the following: (1) Specialty Optical Fibers; (2) Advanced CMOS ICs and (3) optoelectronic and photonic devices. The first set of entries includes examples from the more mature and established class of sensors, such as NIR, mid-IR, and IR absorption techniques, with detection sensitivity in the range of 10s of ppm, with very fast response times. Some examples include $NO_2$ and CO, $C_2H_2$ detection using hollow fibers (see ref. i) and microbore fibers (see ref. ii), respectively. IR absorption studies of $CO_2$ have been pursued using Fourier Transform IR techniques, FTIR (see ref. iii), and NO using Quantum Cascade (QC) lasers as optical probe sources (see ref. iv). The main issues with these systems include the device dimensions, usually in excess of a cubic centimeter, and fiber occlusion, which leads to poor reliability.

Within the second class of basic trace-gas technologies, electrical and electrochemical transducing techniques are included. In this class of sensor, the measured parameter, in the presence of the desired trace gas, is typically a change in resistance, capacitance or current. Fully integrated systems with temperature and relative humidity controls are currently produced by Keibali Corp. and Sandia/H2SCAN for $H_2$ detection using Pd coated MOS capacitors, HEMT, or Schottky diodes with sensitivity down to 02% and milliseconds to seconds response times, with a few years of lifetime claimed (see ref. v). Other porous films of metal-oxides or metal-semiconductors with interdigitated electrode layouts have been used to demonstrate $NO_2$, and $CO_x$ detection below the ppm level (see ref. vi). The major application concern for this class of sensor is claimed to be the partial cross-sensitivity in the presence of other gas species, which can be reduced using high temperatures (thus the integration of micro-hotplates) and noble metals. Also, the response time of few minutes, dependent on the adsorption rates, is higher relative to competing techniques such as galvanic/electrochemical cell based sensors. Test cells, that are commercially available at BW Technologies and RKI Instruments, indicate the presence of a desired trace gas via changes in the measured current, as a result of ox-redox chemical reactions, with long lifetimes and wide dynamic ranges of detection. Their versatility to detect several gases, e.g., $O_x$, $CO_x$, and $NO_x$, becomes an issue since the level of cross-sensitivity to different gases is very high. Porous Si FETs (see ref. vii) and thin films (see ref. viii) which, respectively, reveal a change in current and photoluminescence (PL), have a limitation in terms of saturation, or quenching. These sensors have been used for NO sensing, with sensitivities in the range of <1 ppm levels but the latter are limited by PL recovery time and a chronic PL quench.

Finally, in the third category tabulated in tables 1A and 1B, are listed new nanotechnology approaches such as SERS (Surface Enhanced Raman Spectroscopy), an example of which exploits substrates with silver (Ag) nanoclusters (~100 μm$^2$). These sensors have been currently used for complex molecules detection, e.g., $H_2NO_3$ (see ref. ix), HE, CBW agents (see ref. x) and are presently also being considered for PH and simpler molecular detection (see ref. xi). The limit of the SERS approach appears to be film oxidation, which limits the lifetime and the complexity of readout systems. At present, the level of sensitivity remains relatively high (100 ppm). Hydrogen sensing has also been demonstrated by Zhao et al. (see ref. xii) using white-light reflectance on palladium-gold (PdAu) thin films and by Villatoro/Olpiski et al. (see ref. xiii) using Pd nanotapered fibers at 1.5 μm signal wavelength. These novel techniques seem to be promising, having demonstrated acceptable values in sensitivity, response time, and lifetime in their initial proof-of-concept demonstrations. In addition to the above approaches, there exists relatively mature optical-based (LED) systems for $O_2$ sensing, manufactured at Ocean Optics (see ref. xiv). The underlying principle in this case is based on the quenching of oxygen-sensitive fluorescent dyes, such as Ruthenium (Rt) or porphyrin, embedded in thin films. A step forward is now offered by OLEDs, built at ISTI/Ames Labs and also developed at Tokai University, which are extremely appealing, given that the light source/sensor/controls/detector are integrated into a single miniaturized chip. In these last two examples, the devices are aimed at only one particular molecule. The device applicability and performance limitations of these sensors, which are, at present, still in the development phase, are principally functions of the selection and interaction dynamics of the given surface coatings with the trace-gas(es) of interest.

TABLE 1A (Prior art)

| Configuration | Measured Parameter | Gas Specie | Detection Range | Response Times | Cross-sensitivity |
|---|---|---|---|---|---|
| 0.25 m hollow fiber/microbore | IR abs/NIR abs | $NO_2/CO$, $C_2H_2$ | 10-200 ppm | 0.02-7 s | yes |
| FTIR, 20 cm wdg | IR abs | $CO_2$ | 10-200 ppm | | yes |
| 9 m fiber QC laser | IR absFina | NO | 0.06 ppm | | yes |
| Pd MOS capacitors & HEMT/Schottky diodes | ΔC/C ΔR/R | $H_2$ | 0.2-100% | 75 ms-20 s | yes |
| Galvanic/Electrochemical cells ($cm^3$) | Δl/l by ox-red ox | $O_x$, $CO_xNO_x$ ... | 0-999 ppm | 5-30 s | no |
| Porous Si FET/Thin film | Δl/l/PL | $NO_x$ | 0.1-2 ppm | 10 s m (PL recovery) | yes |
| Porous metal-oxides, metal-semic. IDT electrode | ΔR/R | $NO_2$, $CO_x$ | 0.05-3 ppm | 1-15 m (adsorp. rates) | Partial (high T, noble metals) |
| LED or OLED w/Dye-Thin film (100 μm$^2$) fiber to spectrum | Dye fluorescence quenching | $O_2$ | 0-40 ppm | 1 μs-1 s | yes |
| He—Ne, substr. w/Ag nano clusters (100 μm$^2$), Raman Spectrograph | Wavelength Raman shift Δλ | H2NO3 sarin, HE | ~100 ppm | 30-60 m | yes |
| White Light PdAu thin film reflectance/Pd nanotapered fiber (μm$^2$ × mm)λ = 1.5 μm | ΔR/R/ ΔT/T | $H_2$ | 0.2-4%/ ~10 s | 5-130 s/~10 s | yes |

TABLE 1B (Prior art)

| Configuration | Lifetime | Operational Point | References | Shortfalls |
|---|---|---|---|---|
| 0.25 m hollow fiber/microbore | X (fouling) | Standard | Saito 1992 Prickell 2004 | Dimensions Occlusion Diffusion |
| FTIR, 20 cm wdg | X (fouling) | Standard | Kozodoy 1996 | Dimensions Occlusion Diffusion |
| 9 m fiber QC laser | X (fouling) | Standard | Fetzer 2003 | Dimensions Occlusion Diffusion |

TABLE 1B-continued (Prior art)

| Configuration | Lifetime | Operational Point | References | Shortfalls |
|---|---|---|---|---|
| Pd MOS capacitors & HEMT/Schottky diodes | Few years | T&RH control (MEMS) | Keibali Corp H2scan-SNLA | Cross-sensitivity Irreversibility Time Response Lifetime |
| Galvanic/Electro chemical cells (cm$^3$) | Few mos-few years | T&RH (MEMS) | BW Tectn/RKI Instrum | Cross-sensitivity Irreversibility Time Response Lifetime |
| Porous Si FET/Thin film | Limited (PL red ox) | Standard | Sberveflieri 2006 Sailor 1996 | Cross-sensitivity Irreversibility Time Response Lifetime |
| Porous metal-oxides, metal-semic. IDT electrode | Depend on system | T control: uhotplate (cm$^3$) | Barrettino 2006, Kim 2005 Wang 2003, futurlec.com | Cross-sensitivity Irreversibility Time Response Lifetime |
| LED or OLED w/Dye-Thin film (100 μm$^2$) fiber to spectrum | Few yrs | Std/T&HR control (MEMS) | Ocean Optics/ISTI_Ames Labs/Tokai Un. | Contenders Equipment Lifetime Coating development |
| He—Ne, substr. w/Ag nano clusters (100 μm$^2$), Raman Spectrograph | X (oxid) | Standard | Stokes 2000, 2005 Talley 2004 Yan 2005 | Contenders Equipment Lifetime Coating development |
| White Light PdAu thin film reflectance/Pd nanotapered fiber (μm$^2$ × mm) λ = 1.5 μm | >1 yr | Standard + T&RH control | Zhao 2005 Villatoro 2005 Olpiski 2004 | Contenders Equipment Lifetime Coating development |

SUMMARY OF THE INVENTION

Embodiments of the present invention provide unique configurations for in-situ gas detection, and include miniaturized photonic devices, low-optical-loss, guided-wave structures and state-selective adsorption coatings. High quality factor (Q=λ/dλ>10$^5$ to 10$^{10}$) semiconductor resonators have been demonstrated in different configurations, such as micro-disks, micro-rings, micro-toroids, and photonic crystals with the properties of very narrow NIR transmission bands and sensitivity up to 10$^{-9}$ (change in complex refractive index) (see ref. xv). The devices are therefore highly sensitive to changes in optical properties to the device parameters (e.g., refractive index and absorption) and can be tunable to the absorption of the chemical species of interest. Moreover, appropriate coatings (functionalization) applied to the device enhance state-specific molecular detection.

Additional benefits of this class of sensor include optical fiber compatibility (e.g., remote addressing and probing), high-density device packing, integrability with sources and/or detectors, and enhanced S/N levels using differential techniques, such as common-mode rejection. Fabrication tolerances, optical properties of sensing materials, lifetime and ruggedness constitute other relevant performance metrics that are addressed by this invention (see ref. xvi).

Embodiments of the present invention provide for compact, robust sensors based upon adsorption spectroscopy and integrated transduction mechanisms. This class of sensor is referred to herein as a resonant optical transducer (ROT). The sensors function via changes in their optical properties in response to the state-selective adsorption of a desired species. Special coatings, deposited at critical locations within the sensor structure, provide necessary media for the desired state-selective, trace-gas adsorption as well as for discrimination in the presence of non-critical species. Examples of ROT embodiments include specially coated edge emitting lasers (EELs), vertical cavity surface optical amplifiers (VCSOAs) and vertical cavity surface emitting lasers (VCSELs). The extension of a 1D sensor to a 2D platform results in an array of functionalized and tunable cavities, with application to multiplexed trace-gas detection and discrimination against false alarms. Tables 1C and 1D provide data for embodiments of the present invention for comparison with the prior art shown in Tables 1A and 1B respectively.

TABLE 1C

| Configuration | Measured Parameter | Gas Specie | Detection Range | Response Times | Cross-sensitivity |
|---|---|---|---|---|---|
| TOCs & ROTs | IR abs ΔP/P or Δλ/λ | CO$_x$, NO$_x$, CH$_4$, HCl, HF, O$_2$, H$_2$ | 1-100 ppm | Ns-μs (equipment limited) | yes |

FIG. 1D

| Configuration | Lifetime | Operational point | References | Shortfalls |
|---|---|---|---|---|
| TOCs & ROTs | N/A | Standard + T&RH Control | N/A | New Technology development |

This class of resonant optical transducer, when coated with functionalized films engineered to adsorb specific gas species, can function, e.g., when gases without a significant near infrared (NIR) signature are to be detected. That is, in situations where there is minimal spectroscopic optical interaction cross section with the desired species, the use of adsorption mechanisms can be utilized to advantage. In these cases, the adsorbed species can modify or perturb specific optical properties of a resonant cavity, which can be subsequently detected and sensed via non-resonant optical probes. That is, the optical probe beam does not interact directly with the molecular species, but, instead, probes optical perturbations of the structure resulting from the presence of the given species to be sensed. Therefore, the specific wavelength of the optical sensor is not constrained to a specific optical absorption feature of the molecule.

Hence, as the desired species is adsorbed onto a state-selective coating within the optical sensor, the coating optical properties are modified by the change in the phase (refractive index) and/or absorption (optical loss) of light as it interacts with the now-modified surface coating. The appropriate use of high-gain optical amplifying media and/or lasers can result in trace-gas sensors with high sensitivity and responsivity, owing to the highly nonlinear dependence of these structures to minute phase and/or amplitude perturbations at or near an oscillation threshold. Resonant cavities with high quality factor (Q), or amplification, can enhance the sensitivity of the devices. The operation wavelength of the devices is, in this case, independent of the gas and only a very small footprint is necessary. Nevertheless, a tunable source provides several advantages over a fixed-wavelength optical probe beam, especially in the presence of systematic errors.

Regarding the probe beam, an optical source with a 30-50 nm wavelength tuning range is beneficial to track the resonance of the optical amplifier when the trace-gas molecules infiltrate or bond to the specific coating and change the resonance condition by effectively changing the optical path. In addition to monitoring peak-amplitude variations of the fixed, initial cavity resonance, source tunability can circumvent various systematic effects, as well as determine the optimal wavelength overlap of the probe beam with the Fabry-Perot modes of the optical cavity. By analogy, in the case of VCSELs, tunability provides similar benefits, in addition to molecular detection via resonant photon interactions, as discussed below.

BRIEF DESCRIPTION OF THE DRAWINGS

The accompanying drawings, which are incorporated into and form a part of the disclosure, illustrate embodiments of the invention and, together with the description, serve to explain the principles of the invention.

FIG. 7 shows results of the output optical spectrum of a VCSEL as function of voltage bias applied to a longitudinally moveable, laser output mirror.

DETAILED DESCRIPTION OF THE INVENTION

Figure 1:
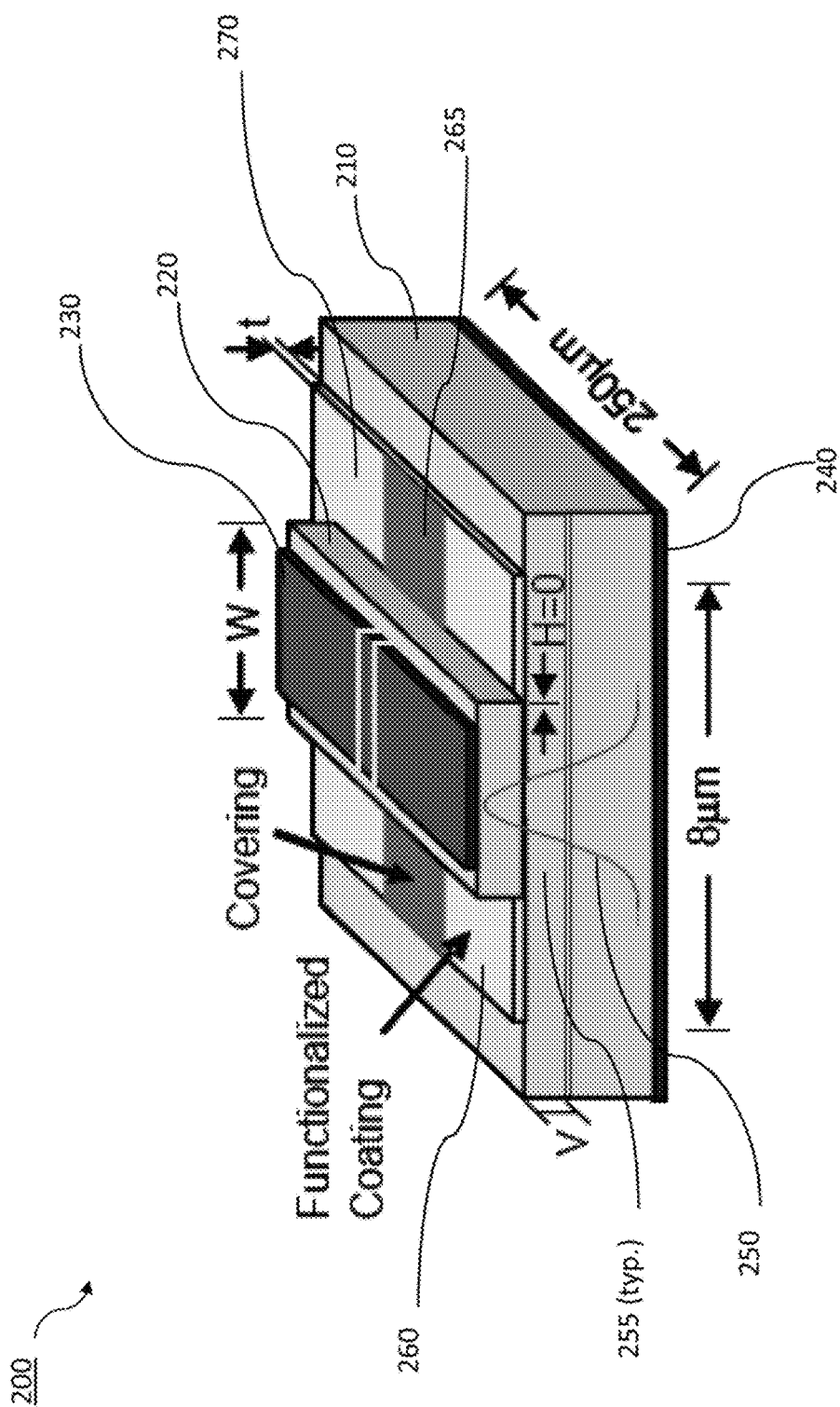
FIG. 1 depicts an embodiment using an edge-emitting laser (EEL), with lateral functional coatings as a trace-gas sensor.

One embodiment of a present ROT is shown in FIG. 1, the basic structure of which is a semiconductor-based edge-emitting laser, EEL 200. The basic EEL, which is well known in the art, is augmented with a state-selective thin-film functionalized adsorption layer, thereby resulting in the trace-gas sensor. The EEL is comprised of a substrate, 210, upper (gain) guiding ridge layer 220, and top and bottom contacts, 230 and 240, respectively, for biasing. In some cases, the top contact can be partitioned, so that different regions within the laser can possess differing amounts of optical gain or loss. The basic guided-wave optical mode, 250, is confined vertically by the basic waveguide structure and laterally, via gain guiding. The EEL optical cavity consists of a pair of Fresnel reflective air/semiconductor interfaces, 255, formed at the front and rear substrate facets, respectively, normal to the optical axis. The semiconductor materials and structure of the basic laser are well known in the art. As an example, the EEL laser can be comprised of Group III-V materials, e.g., InAs, InP and GaAs, and its ternary and quaternary alloys (e.g., InGaAs and InGaAsP, respectively); and the gain medium can be configured in a variety of architectures, an example of which is a double quantum-well structure (DQW) using similar materials.

In this embodiment, a set of functionalized surface regions, 260 and 270, respectively, are each coated with a suitable state-selective adsorptive thin-film layer. These coatings are deposited on the upper surface of the EEL, and positioned on either side of the ridge guiding layer, 220. By changing the coating, different gases can be detected with a well-defined selectivity and specificity as a function of the coating material. During operation, as the desired species is adsorbed by the thin film, the optical properties of the material will be modified, such as its refractive index and/or absorption. These trace-quantity induced thin-film optical perturbations will, in turn, affect the output of the EEL, in terms of its laser output power, output spectrum and modal characteristics. The sensitivity to the adsorbed material is enhanced by the highly nonlinear dependence of the laser properties to the optical cavity characteristics. In essence, the internal laser photons traverse the optical cavity multiple times (100s to 1,000s of traversals, depending on the specific laser design), thereby probing the modified cavity parameters in a like manner, and, thusly, effectively amplifying the sensitivity of the sensor. Various regions on the coatings can be masked via optional coverings, 265, as may be deemed necessary for a given structure.

An example of a coating, with application to the detection of trace quantities of $H_2$ gas, is a thin film of either Pd or Pt. The optical and electrical properties of these materials change in the presence of $H_2$ which can be detected even in a background of atmospheres of $N_2$. In a separate set of experiments, ellipsometric measurements were performed on Pd and Pt thin films to quantify the complex index of refraction at various optical wavelengths of interest, with and without the presence of $H_2$. These measurements enable more accurate quantitative information to be obtained using the thin-film coated trace-gas sensors, discussed herein. In addition, they provide more accurate data as input to the sensor simulations so that their performance can be optimized.

Figure 2:
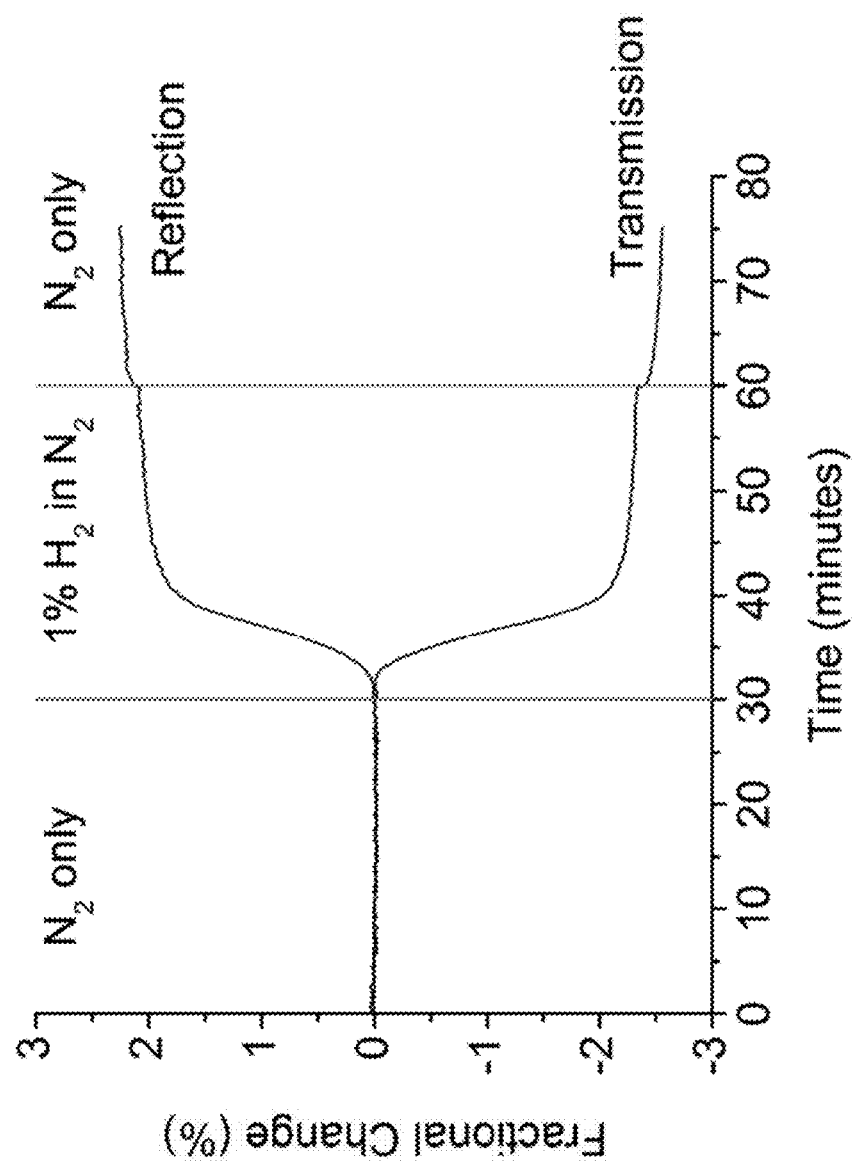
FIG. 2 shows results of a simulation depicting the optical mode profile of an EEL output beam.

FIG. 2 shows data of the measured fractional change in reflection (FCR), $\Delta R/R_0$, and transmission (FCT), $\Delta T/T_0$ for an optically thin Pt 11.83 nm film, in the presence of $H_2$. The fractional change technique is beneficial because it normalizes out collection efficiency proportionality factors. The steady state FCR and FCT values for 1% $H_2$ were 2.06% and −2.32%, respectively. A Pd 26.94 nm film had a similar response with FCR=1.33% and FCT=−1.42%. The anomalous reflectance increase in optically thin films can be attributed to reflections from multiple interfaces. For the thick films, statistically significant changes were not observed.

The Pt and Pd thin-film rise times were quite different; 10 minutes and 10 seconds, respectively. After the $H_2$ is shut off, the reflection and transmission for both films begin moving away from the baseline. This behavior is under investigation. With the measured 1550 nm values for n and κ for each film, the spectrally averaged FCR and FCT were simulated for $\Delta n=0.001$ and $\Delta \kappa=0.001$ using the transmission matrix technique. Assuming linear dependencies, the combination of $\Delta n$ and $\Delta \kappa$ that yield the measured FCR and FCT can be solved algebraically from a 2×2 matrix. Estimates of $\Delta n$ and $\Delta \kappa$ made this way were very close to the solutions obtained from iterative searching. For 1% $H_2$ in $N_2$, we find $\Delta n=-0.089$ and $\Delta \kappa=0.181$ for the Pt 11.8 3 nm film, compared to $\Delta n=-0.033$ and $\Delta \kappa=0.067$ for the Pd 26.94 nm film. The increase in extinction coefficient is unexpected given previous discussions and trends for Pd films. Additional experiments are needed to confirm this trend and the parameter extraction technique. Nonetheless, these measurements provide useful input to the modeling and simulation of the $H_2$ trace-gas sensors.

The performance of the embodiment shown in FIG. 1 was modeled using a numerical simulation code. As a specific example of an EEL sensor, a laser with a graded-index separate confinement heterostructure (GRINSCH) configuration was considered, using a standard double quantum well (DQW) structure. Lasers without lateral surface coatings have been previously fabricated and thoroughly characterized and modeled. For this choice of material and geometry, the laser wavelength varies from 950-970 nm, depending on bias and temperature. The EEL geometry that was modeled is a multiple section 2 μm×250 μm (EEL) with a 50 nm thick Pd surface coating that is located 100 nm above the active region and extends 3 μm laterally on either side. Thus, the total sensor width is 8 μm (see FIG. 1 for labeling of the dimensions). The optical mode has a small overlap, $\Gamma_{Pd} \approx 1 \times 10^{-4}$, with this thin coating. $H_2$ gas reacts with Pd to form PdH thereby reducing the internal loss seen by the laser mode, $\alpha_i$, from 58 cm$^{-1}$ at a rate of 0.03 cm$^{-1}$ per 100 ppm of $H_2$ for our example sensor. Thus, the laser's output power increases rapidly in response to the amount of adsorbed $H_2$.

Figure 3:
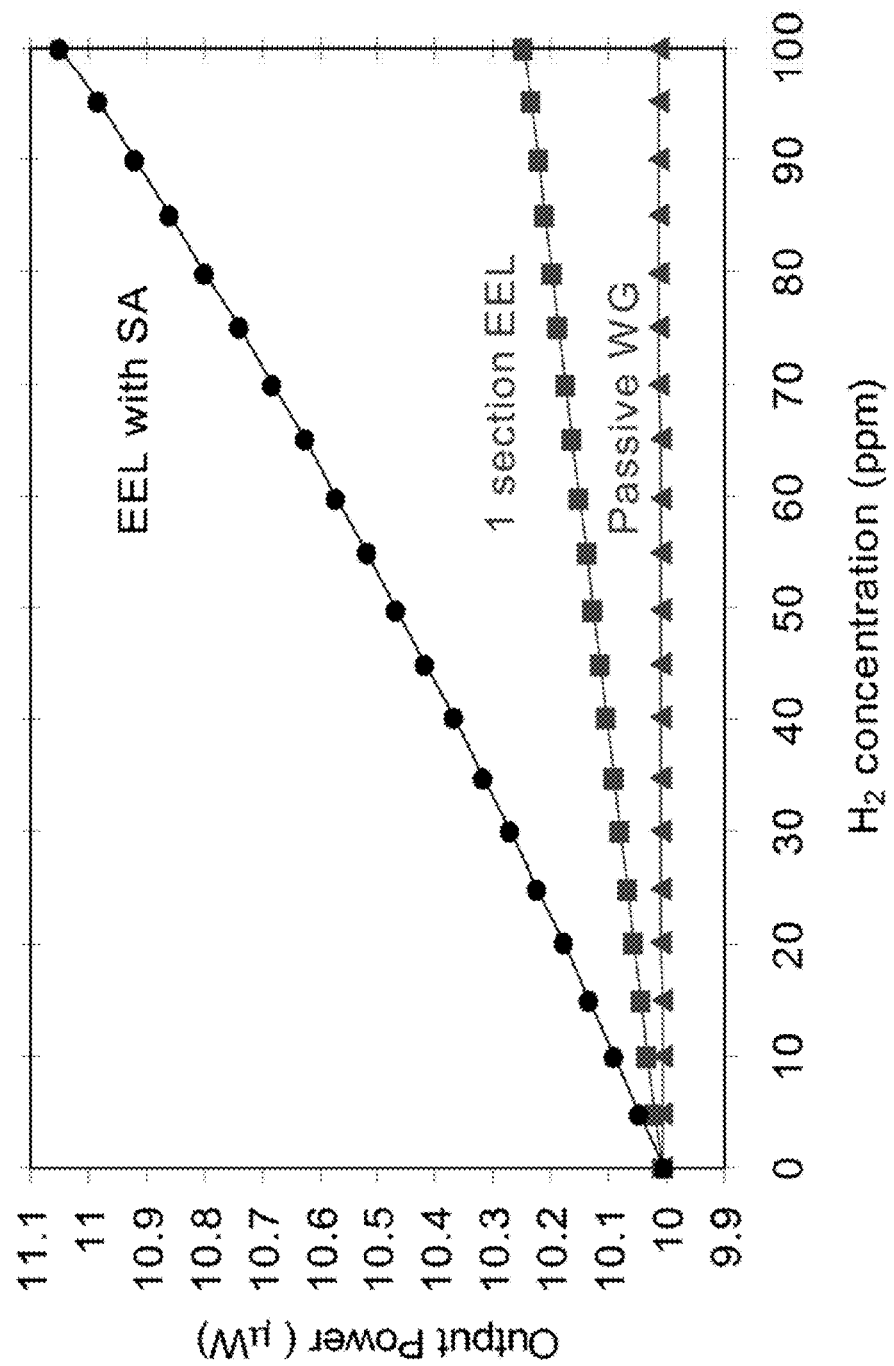
FIG. 3 shows results of a measurement of fractional changes in the optical reflection and transmission coefficients of a 11.83 nm thin film of Pt in the presence of $N_2$ and $H_2$ gases.

FIG. 3 shows results of a simulation to model the laser sensor. A 1-D rate equation model, previously verified against experimental L-I data, was used to calculate the response for L=250 μm, W=2 μm, V=100 nm, and t=50 nm for three types of Pd-coated sensors: a passive waveguide (WG), a single section EEL, and a multiple section EEL, the latter of which includes a 37.5 μm long unbiased saturable absorber with ≈15% optical absorption. (FIG. 1 shows the dimensional labeling.) For a fair comparison, we adjust the biases so that the sensor's output optical power is fixed at 10 μW for zero $H_2$. It is also assumed that laser output power measurement has an instrument uncertainty of $\approx 10^{-3}$.

For this set of parameters, the predicted limits of detection (LODs) for the three structures were 138 ppm, 4 ppm, and 1 ppm, respectively. The passive WG requires 43 μW of input optical power, whereas the EELs need no input optical power but use 8 mW and 13 mW, respectively, of electrical power, given an operation voltage of 1.5 V. Shorter cavity lengths used less power but had higher minimum detection limits (MDLs). The resonant cavity of the EEL provides a strong nonlinearity in the sensor response, i.e., the lasing knee, and thereby reduced the LOD compared to the passive WG. The saturable absorber further amplifies this lasing knee nonlinearity according to the gain-lever effect.

Figure 4:
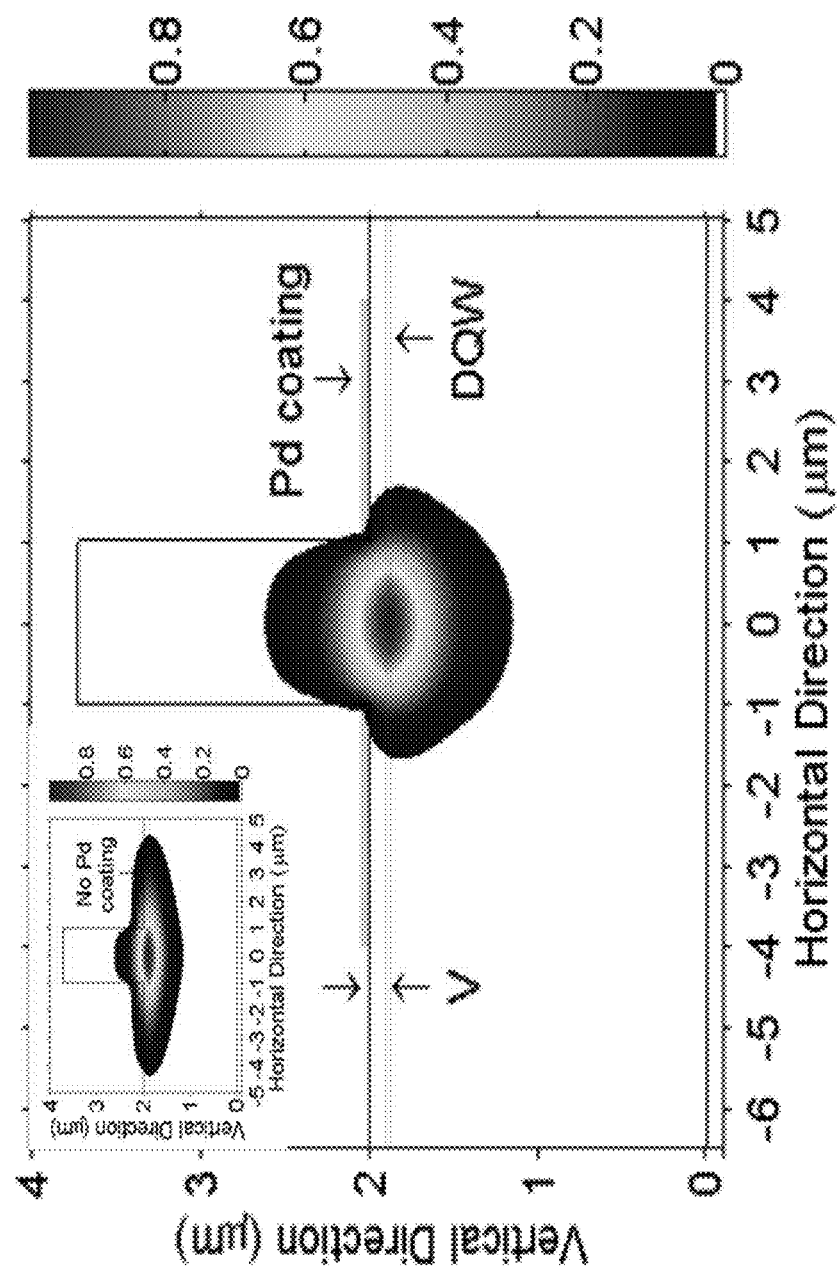
FIG. 4 shows simulated $H_2$ trace-gas sensor responses for a Pd-coated passive waveguide (WG), a single-section EEL, and a multi-section EEL.

The simulation also provided spatial information as to the guided-wave mode supported by the EEL structure. FIG. 4 shows a typical "pear shaped" spatial mode profile for the case W=2 μm and $t_{Pd}$=50 nm and the inset shows $t_{Pd}$=0 nm. Both have elliptical central field contours, but the contours at the field tails for $t_{Pd}$=50 nm are significantly squeezed in by the Pd coating, despite the very small modal overlap. The high sensitivity of the spatial-mode dependence on Pd coating is, most likely, due to the optical cavity losses experienced by the guided-mode field in the presence of the thin film. Given the dependence of the mode profile as a function of the adsorbing coating, a real-time measurement of changes in the spatial-mode pattern may, in fact, provide additional evidence regarding the presence of trace-gas species.

These chip-scale EEL-based sensors offer high sensitivity, wide dynamic range, inline integration with photodetectors and 2-D scalability for drift compensation and for detection and identification of multiple species. For maximal sensitivity, a large spatial-mode field overlap with the coating is needed. This can be achieved with a narrow ridge, a thick coating layer, zero horizontal distance between ridge and coating, and a small vertical separation between coating and active region. For the 8 μm×250 μm $H_2$ sensor with W=2 μm, V=100 nm, t=50 nm, a LOD of 1 ppm is predicted.

Returning to FIG. 1, the absorption layer(s) can be deposited at other locations on the EEL and in various patterns, with the proviso that the optical parameters of the EEL output and/or the cavity mode pattern, 250, is measurably altered as a result of the adsorption of the desired gas specie(s). The EELs can be configured using differently designed optical resonators in place of (broadband) Fresnel reflective interfaces. Examples of different EEL resonators include those formed using distributed Bragg reflecting (DBR) gratings as narrowband end mirrors or, distributed Bragg feedback grating structures (DFB), as well as microtoroidal and ring resonators. The DBR and DFB lasers can provide single longitudinal-mode operation, which may increase the sensitivity of the resultant EEL gas sensor, as well as provide for enhanced performance detection via common-mode rejection techniques (using closely situated pairs of coated and uncoated EELs, on a common substrate).

A laser with a suitable output wavelength can be designed so that the quantum levels of the desired species (or, isotope, thereof) to be sensed can be resonant with the optical mode. In this case, a single EEL can provide a sensor with a dual-detection modality: (1) simultaneous resonant optical detection of the desired trace species via direct optical interaction of the molecule of choice with the laser photons and (2) broadband detection of the trace species via state-selective adsorption of the molecule of choice, as manifested by non-resonant changes in the laser output characteristics, such as cavity mode, wavelength, polarization, etc.

Figure 5:
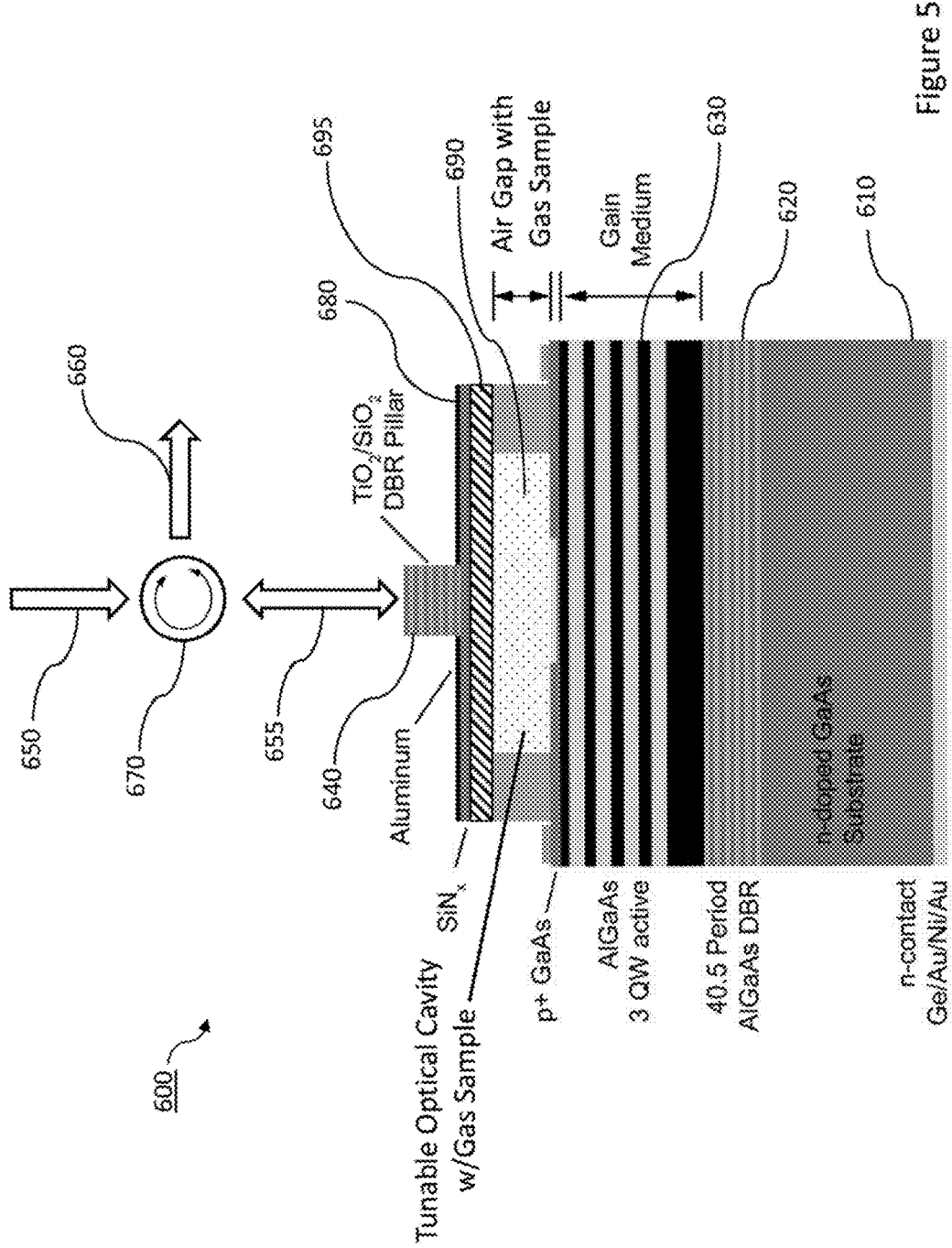
FIG. 5 depicts an embodiment using a vertical cavity surface optical amplifier (VCSOA) with an additional oxide layer in the mirror stack to detect adsorbed gases.

FIG. 5 shows an embodiment of a trace-gas sensor using a specially coated vertical cavity surface optical amplifier (VCSOA), 600. The basic VCSOA is similar in its configuration to that of a conventional vertical cavity surface emitting laser (VCSEL), except for the fact that the VCSOA is not an oscillator, but, instead, a multi-pass optical amplifier. In essence, the VCSOA is a VCSEL that operates below the laser threshold condition. Typically, the VCSOA is fabricated using either a lower gain and/or a lower mirror reflectivity relative to a VCSEL for a given bias.

The VCSOA and the VCSEL devices are well known in the art. In general, both devices are comprised of a substrate 610, with an internally fabricated single or multi-layer reflecting mirror, 620, whose reflectivity is 100%. An internal gain medium, 630, typically a semiconductor based multi-layer structure, is grown onto the mirror 620. In most cases, an input/output mirror, in the form of a partially transmitting mirror, 640, is subsequently grown above the gain medium, completing the basic structure (for simplicity, electrical contacting layers and various buffer layers are not described, as they are well known in the art).

During operation, an optical interrogation beam, 650, is incident upon the VCSOA. The incident beam interacts with the optical cavity, resulting in an amplified output beam, 660. Owing to the geometry of the device, the counter-propagating input and output beams, 655, overlap in space. Typically, an optical circulator, 670, is employed to distinguish the input and output beams.

In the present embodiment, the basic VCSOA is augmented through the use of a vertically displaced, deformable membrane, 680, typically, $SiN_x$ with a coating of Al, upon which the input/output coupling mirror, 640, is grown. One function of the deformable membrane/mirror is to vary the optical cavity length, and, therefore, to control the spectral properties of the VCSOA. For a given interrogation wavelength, the cavity can therefore be tuned so that the Fabry Perot mode(s) within the cavity are in resonance with the input probe beam for maximum sensitivity of the sensor.

The presence of the vertically displaced output mirror, 640, results in an air gap, 690, formed between the upper surface of the basic structure and the inner-cavity surface of the output mirror. During operation, the gas sample to be analyzed is allowed to flow into the intra-cavity gap, 690.

The trace-gas sensor also consists of a metal oxide coating layer, 695, grown onto the inner-cavity surface of the membrane (680)-mirror (640) structure. This oxide layer is selected to modify the effective coupling-mirror reflectivity in the presence of the trace-species to be sensed. The change in reflectivity is due to a change in the refractive index and/or optical absorption in the coating layer as the trace-gas is adsorbed in the film. This change in the reflectivity, as a result of the presence of the trace-gas, can be detected by measuring changes in the VCSOA output beam, 660, including changes in the optical power and/or shifts in the output spectrum. Examples of adsorbing materials and coatings include $WO_3$, $SnO_2$, PdO, ZnO, and porous Si. The optical properties of these coatings are modified in the presence of a variety of trace gases, including $NO_x$, CO, $H_2S$ and $Cl_2$. By changing the coating, different gases can be detected, with varying degrees of selectivity and specificity.

Figure 6:
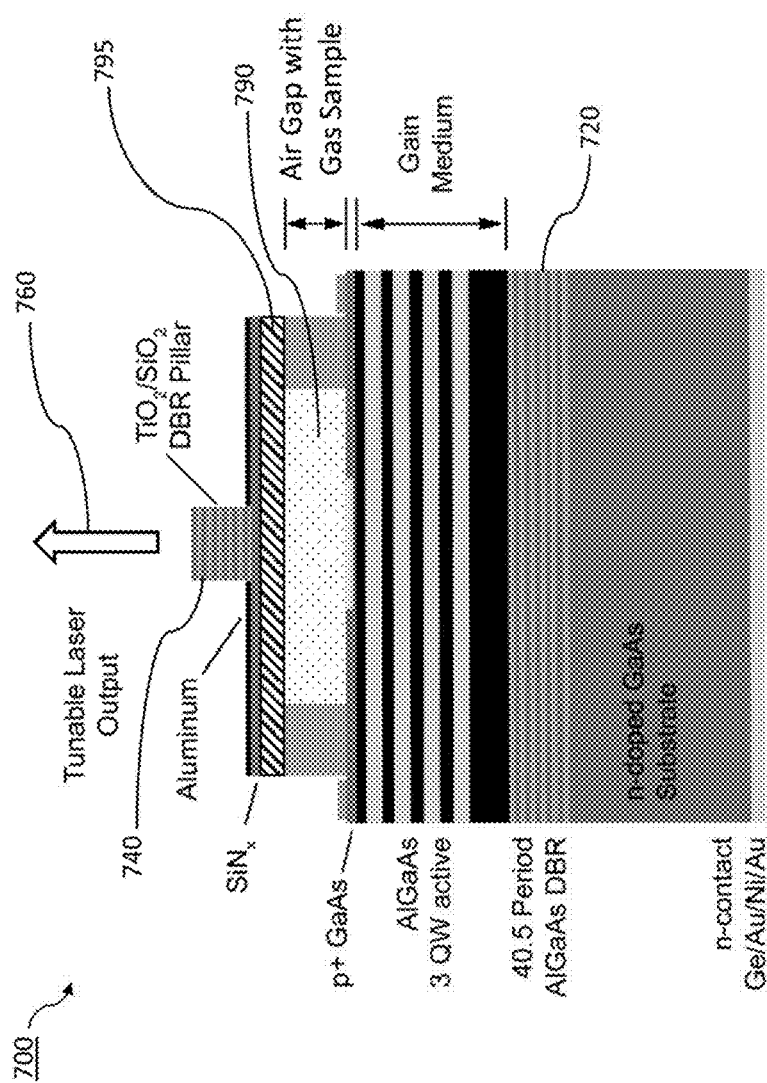
FIG. 6 depicts an embodiment using a vertical cavity surface emitting laser (VCSEL) with an additional oxide layer in the mirror stack to detect adsorbed gases.

Turning now to FIG. 6, an embodiment using a VCSEL, 700, is shown, that combines two different, yet, complementary, trace-gas detection modalities into a single device: (1) sensing changes in the properties of an optical device via non-resonant adsorption of a given species within the cavity and (2) sensing resonant photon interactions of the intracavity optical beam directly with a specific molecular absorption feature of the trace-gas species. The first modality has been described above, whereby indirect optical measurements are performed to infer the presence of a given adsorbed species in an optical resonator. The second modality, which complements the first approach, is a form of NIR absorption spectroscopy performed within a laser cavity.

The basic configuration, as shown in FIG. 6, is that of a VCSEL, with a vertically displaced, membrane-mounted output mirror, 740, an intra-cavity air gap, 790, and an internal adsorption oxide layer, 795. Hence, the basic configuration is similar to that of the VCSOA embodiment (see, e.g., FIG. 5). As discussed above, the VCSEL is an optical oscillator (a laser), and as such, generates an output optical beam, 760. Therefore, no external interrogation beam is required, as the optical oscillator provides an effective probe beam within the cavity. Since the oscillating beam passes through the air gap multiple times, the presence of a trace gas can be sensed via changes in the output beam, as before. However, the output beam changes can be induced by either cavity perturbations resulting from changes in the internal optical coating, 795, and/or by direct optical absorption with the gas sample itself. The presence of a trace-gas can therefore be inferred by changes in the VCSEL laser output beam, including its output power and its output spectrum. Furthermore, the VCSEL operating wavelength can be tuned via changes in the vertical displacement of the moveable mirror. Thus, the VCSEL trace-gas sensor can be described as a wavelength tunable, multi-pass cell with optical gain.

In operation, the laser is electrically driven above threshold, with the gas sample allowed to flow through the air gap, 790. The presence of the desired trace-gas spoils the gain-loss balance necessary for lasing by increasing the absorption losses within the cavity, either by resonant coupling with the gas molecule within the air gap and/or by non-resonant optical cavity changes induced by adsorption of the gas into the internal oxide layer, 795. In either case, the high-Q of the VCSEL structure enhances the sensing by adsorption and/or absorption, as the light is reflected multiple (>100) times within the resonant cavity, formed on one end by the external membrane distributed Bragg reflecting (DBR) mirror, 740, and on the other end by the internal distributed DBR mirror, 720. During operation, the lasing power and/or output spectrum can be monitored remotely by transmission through an optical fiber or directly by an integrated detector.

Figure 8A:
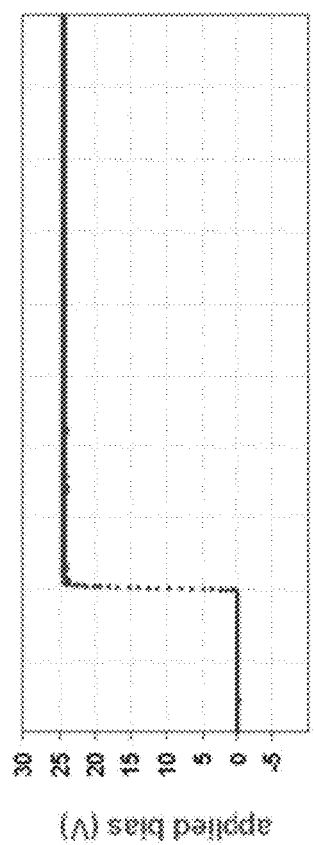
FIG. 8A shows a plot of a voltage waveform, as applied to a membrane mirror to evaluate the transient response of a tunable VCSEL.
Figure 8B:
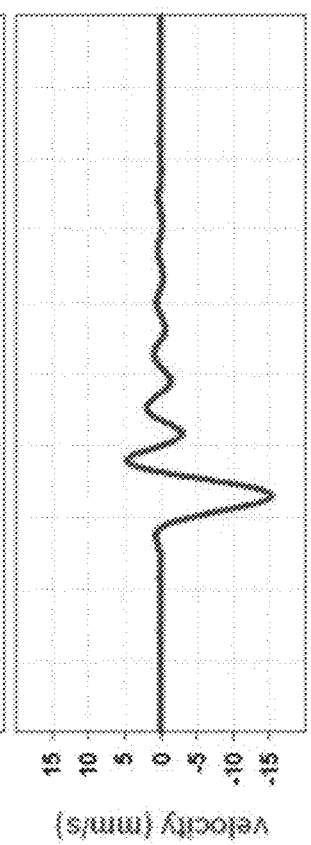
FIG. 8B shows a measurement of the transient velocity response of a VCSEL membrane mirror in the presence of the applied drive waveform shown in FIG. 8A.
Figure 8C:
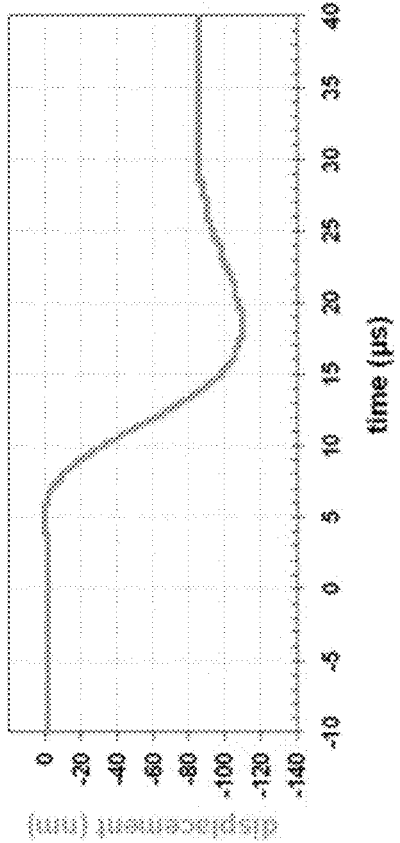
FIG. 8C shows a measurement of the transient displacement response of a VCSEL membrane mirror in the presence of the applied drive waveform shown in FIG. 8A.

A VCSEL with a moveable membrane-based output coupler was fabricated and evaluated in terms of its spectral properties as well as its temporal response to transient changes in the optical cavity length. FIG. 7 shows results of the measured dependence of the VCSEL output spectrum for different values of a bias control voltage, as applied to the moveable mirror membrane. As the membrane is electrostatically displaced, the output spectrum is observed to change correspondingly, shifting to shorter wavelengths as the cavity length decreases (increasing bias voltages). The multiple spectral features for each measured spectral scan are attributed to the presence of the VCSEL's multiple longitudinal modes, given the cavity design parameters. Figure A8-8C show results of the temporal response time of the moveable membrane. FIG. 8A shows the transient control voltage, as applied to the membrane. The response of the membrane in the presence of this transient signal is shown in FIGS. 8B and 8C, which, respectively, display measurements of the membrane velocity and displacement. The membrane response time is observed to be in the range of ≈10 µsec under these conditions.

Figure 9:
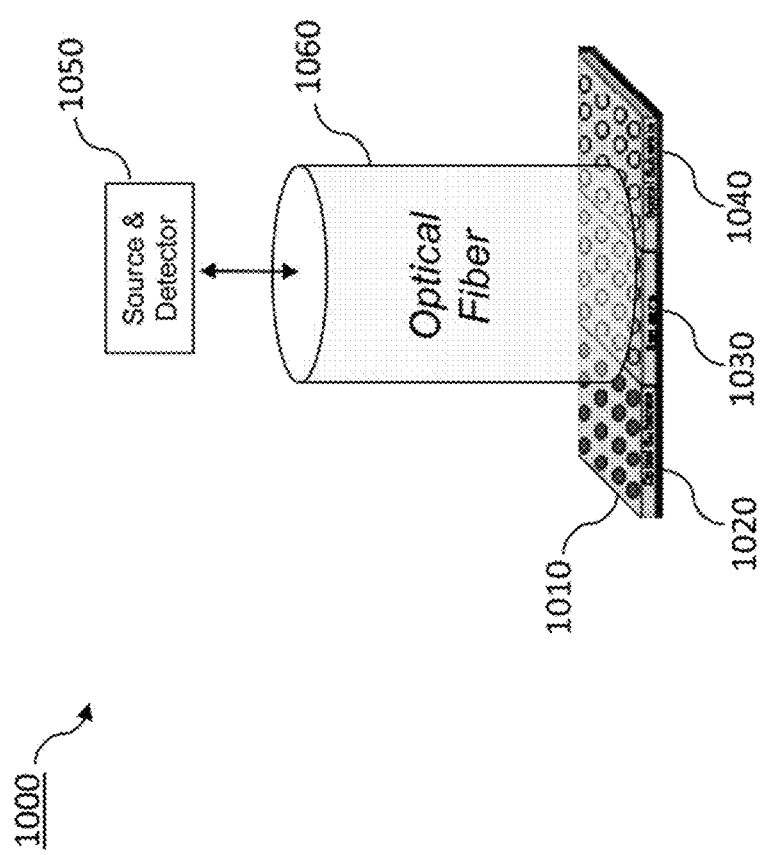
FIG. 9 depicts a system-level embodiment of a trace-gas sensor 2D-array using an optical fiber as a remote optical interrogation probe.
Figure 10:
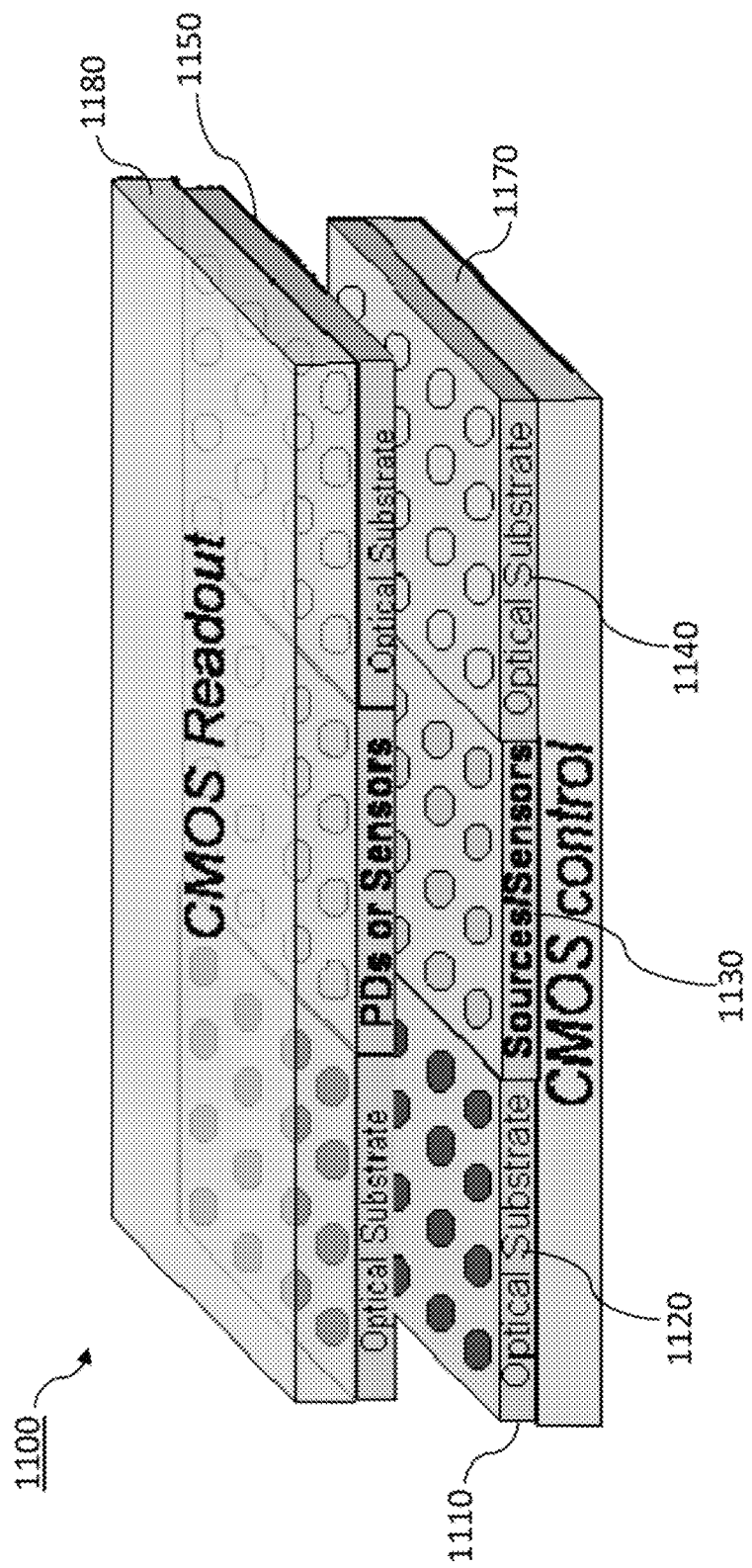
FIG. 10 depicts a system-level embodiment of a trace-gas sensor array using a 2D CMOS array for parallel sensor control and readout.

FIGS. 9 and 10 show two different systems implementations of the trace-gas sensor device, 1000 and 1100, respectively. In each embodiment, a 2D array of resonant optical transducers is depicted in the figures, as indicated by 1010, and 1110, respectively. In FIG. 9, a remote optical fiber interrogation approach is shown. In this embodiment, the sensor package, 1010, can be placed at one location, and the optical sources and/or detector components, 1050, can be located elsewhere, using an optical fiber, 1060, as an optical link. In FIG. 10, a compact 2D sensor/readout approach is shown, using CMOS technology for the sensor control functions, 1170, and, additionally for 2D parallel readout and pre-processing functions, 1180. The geometry in the latter case is symmetrical, in that the sensor and readout arrays are identically configured, forming a 2D array of free-space optical interconnects linking the sensor and the interrogator arrays.

In both systems implementations, each 2D array is partitioned into three regions, 1020, 1030 and 1040 in the case of FIG. 9 and 1120, 1130 and 1140 in the case of FIG. 10. Each of the three respective regions consists of sensors designed to respond to a unique trace species. The presence of multiple sensors for each species provides redundancy in terms of graceful degradation, as well as the potential to provide for minimal false alarm rates, systematic errors, etc.

REFERENCES (INCORPORATED HEREIN BY REFERENCE)

i. L. Goddard, T. Bond, J Kallmna, "Rapidly Reconfigurable All-Optical Universal Logic Gate" Provisional Patent Application Ser. No. 60/872,309.
ii. M. Saito et al., "Spectroscopic gas sensing with infrared hollow waveguide", Proc SPIE, v. 1796, p. 231, 1992.
iii. G. Prickell et al., "Random-hole optical fiber evanescent-wave gas sensing", Opt. Exp., v. 29, p. 1476, 2004.
iv. R. L. Kozodoy et. al, "Small-bore hollow waveguide infrared absorption cells for gas sensing", Appl. Spec., v. 50, p. 415, 1996.
v. G. J. Fetzer et al., "Midinfrared laser absorption spectroscopy in coiled hollow optical waveguides", Proc. SPIE, v. 4957, p. 124, 2003.
vi. K. T. Kim et al., "Hydrogen gas sensor using Pd nanowires electro-deposited into anodized alumina template", IEEE Sensor Journal, v. 6, p. 509, 2006; C-C Chen et al., "Pd-oxide $Al_{0.24}Ga_{0.76}As$ (MOS) high electron mobility transistor (HEMT)-based hydrogen sensor", IEEE Sensor Journ., v. 6, p. 287, 2006; www.kebaili.com; www.makelengineering.com; www.h2scan.com.
vii. D. Barrettino et al., "CMOS monolithic metal-oxide gas sensor microsystems", IEEE Sensor Journ., v. 6, p. 276, 2006; I. J. Kim et al., "Sensitivity enhancement for CO gas detection using a $SnO2-CeO2-PdOx$ system", Sens&Actuat. B, v. 105, p. 825, 2005; S. H. Wang, "Nano-crystalline tungsten oxide $NO_2$ sensor", Sens&Actuat. B, v. 94, p. 343, 2003; www.futurlec.com.
viii. G. Barillaro et al., "Low-concentration $NO_2$ detection with an adsorption porous silicon FET", IEEE Sensor Journ., v. 6, p. 19, 2006.
ix. J. Harper et al., "Detection of nitric oxide and nitrogen dioxide with photoluminescence porous silicon", Anal. Chem., v. 68, p. 3713, 1996.
x. D. L. Stokes et al., "Surface-enhanced-Raman scattering-inducing nanoprobe for spectrochemical analysis" Appl. Spect. v. 58, p. 292, 2004.
xi. F. Yan et al., "SERS detection of CB agent simulants", Sensor. Journ, v. 5, p. 665, 2005.
xii. C. E. Talley, "Intracellular pH sensor based on SERS", Anal. Chem, v. 76, p. 7064, 2004.
xii. Z. Zhao et al., "All-optical H2 sensor based on high alloy content Pd thin film", Sens&Actuat. B, v. 113, p. 532, 2006.
xiv. J. Villatoro et al., "Fast detection of $H_2$ with nano fiber tapers coated with ultra thin palladium layers", Opt. Lett., v. 13, p. 5087, 2005; Z. Opilski et al., "Determination of the optical properties of thin palladium layers and their application in optical hydrogen sensors", Proc. SPIE, v. 5576, p. 208, 2004.
xv. www.oceanoptics.com V. Savvate'ev et al., "Integrated organic light emitting device/fluorescence chemical sensor", Appl. Phys. Lett., v. 81, p. 4653, 2002, www.isensortech.com/; K. Mitsubayashi et al., "Bio-optical gas-sensor (sniffer device) with a fiber optic oxygen sensor", IEEE Conf. Proceed., p. 213, 200.2
xvi. A. C. Pipino et al., "Evanescent wave cavity ring down spectroscopy with a TIR minicavity", Rev Sci. Instrum. V 68, p. 2978, 1997; M. Borselli et al., "Measuring the role of surface chemistry on SI microphotonics_Appl. Phys. Left., v. 88, p. 131114-1, 2006; E. Krioukov et al. "Sensor based on an integrated optical microcavity", Op. Lett, v. 27, p. 512, 2002; D Armani et al., "Ultra-high-Q toroid microcavity on a chip", Nature, v. 421, p. 925, 2003; H. Ouyang et al., "Biosensing with one dimensional photonic bandgap structure, Proceedings SPIE v. 5511, p. 71, 2004; S. E. Létant et al., U.S. Pat. No. 6,785,432 B2; www.agilent.com.
xvii. I. Puscasu et al., "Extraordianry emission form 2-dimensional plasmonic-photonic crystal", Journ. Appl. Phys., v. 98 p 13531, 2005; www.ion-optics.com.
xviii. 2005 Goddard, L., Bond, T. C., Kallman, J. S., 2006, Reconfigurable all-optical universal logic gate: (invited) SPIE Optics East 2006, Boston, Mass.; Pocha, M., Bond, T. C., et al., 2005, Gain lever characterization in monolithically integrated diode lasers: Proceeding SPIE West 2005, San Jose Calif.; R. Welty, R. J., Bond, T. C., et al., 2005, Integrated laser with low-loss high index-contrast waveguides for OEICs: Proceeding SPIE West 2005, San Jose; M. A. Lowry, M. E., Bennett, C. V., Vernon, S. P., Bond, T. C., et al., 2003, RadSensor: Xray detection by direct modulation of an optical probe beam: Proc. SPIE, Optics & Photonics, Optical Engineering and Instrumentation; Bond, T. C., et al., 2003, Time-domain (TD) tools for the investigation of gain-quenched laser logic (GQLL): 2003 International Semiconductor Device Research Symposium, Washington, D.C.
xix. Opilski Z, "Determination of the optical parameters of thin palladium layers and their application in optical hydrogen sensors", SPIE Proceed., v. 5576, p. 208, 2003.
xx. A. M. Armani, K. J. Vahala, Heavy water detection using ultra-high-Q microcavities, Opt. Lett. 31, pp. 1896-1898, 2006.

The foregoing description of the invention has been presented for purposes of illustration and description and is not intended to be exhaustive or to limit the invention to the precise form disclosed. Many modifications and variations are possible in light of the above teaching. The embodiments disclosed were meant only to explain the principles of the invention and its practical application to thereby enable others skilled in the art to best use the invention in various embodiments and with various modifications suited to the particular use contemplated. The scope of the invention is to be defined by the following claims.

We claim:

1. A resonant optical transducer, comprising:
a first electrical contact layer;
a substrate in operative contact with said first electrical contact layer, said substrate including an internally fabricated mirror;
an active gain medium in operative contact with said substrate;
a second electrical contact layer in operative contact with said gain medium;
two pillars in operative contact with said second electrical contact layer;
a top layer supported by said pillars, wherein said top layer together with said second electrical contact layer and said pillars, forms an optical cavity having an intra-cavity gap, wherein said top layer includes a state selective oxide layer in operative contact with a reflective layer; and
a mirror in operative contact with said top layer.

2. The resonant optical transducer of claim 1, further comprises a deformable membrane layer in operative contact with and located between said state selective oxide layer and said reflective layer.

3. The resonant optical transducer of claim 1, wherein said first electrical contact layer comprises a first dopant, the ROT further comprises a doped layer between said second electrical contact layer and said gain medium, wherein said doped layer comprises a second dopant, wherein one of said first dopant or said second dopant comprises an n material and the other comprises a p+ material.

4. The resonant optical transducer of claim 1, wherein each pillar of said two pillars comprises electrically insulating material.

5. The resonant optical transducer of claim 4, wherein said electrically insulating material comprises a dielectric material.

6. The resonant optical transducer of claim 1, wherein said first electrical contact layer is an n-contact layer.

7. The resonant optical transducer of claim 6, wherein said n-contact layer comprises Ge/Au/Ni/Au.

8. The resonant optical transducer of claim 1, wherein said substrate is an n-doped GaAs substrate.

9. The resonant optical transducer of claim 1, wherein said internally fabricated mirror is a multi-layer mirror.

10. The resonant optical transducer of claim 9, wherein said multi-layer mirror is a 40.5 period AlGaAs distributed Bragg reflector.

11. The resonant optical transducer of claim 10, wherein said DBR comprises a reflectivity of $\approx 100\%$.

12. The resonant optical transducer of claim 1, wherein said active gain medium comprises a semiconductor based multi-layer structure.

13. The resonant optical transducer of claim 12, wherein said semiconductor based multi-layer structure is selected from the group consisting of an AlGaAs quantum well, InGaAs and InGaAsSb.

14. The resonant optical transducer of claim 1, wherein said second electrical contact layer comprises p+ GaAs.

15. The resonant optical transducer of claim 1, wherein said state selective oxide layer comprises metal oxide.

16. The resonant optical transducer of claim 1, wherein said deformable membrane comprises $SiN_x$.

17. The resonant optical transducer of claim 1, wherein said reflective layer comprises aluminum.

18. The resonant optical transducer of claim 1, wherein said mirror comprises a $TiO_2/SiO_2$ distributed Bragg reflector pillar.

19. The resonant optical transducer of claim 1, wherein said state selective oxide layer comprises oxide material selected from the group consisting of $WO_3$, $SnO_2$, PdO, ZnO and porous Si.

20. The resonant optical transducer of claim 1, wherein said ROT comprises at least one opening to allow gas to enter said optical cavity.

21. A method, comprising:
providing the resonant optical transducer (ROT) of claim 1;
operating said ROT below its laser threshold condition;
coupling an optical interrogation beam into said optical cavity such that said beam oscillates therein and an amplified output beam is produced;
allowing a gas sample to flow into said intra-cavity gap, wherein said state selective oxide layer comprises oxide material selected to modify the effective coupling-mirror reflectivity of said reflective layer in the presence of a trace-species to be sensed; and
measuring changes in said output beam to determine if said trace-species is present within said optical cavity.

22. The method of claim 21, wherein said changes are relative to said optical interrogation beam.

23. The method of claim 21, wherein said changes include changes in the optical power and/or shifts in the spectrum of said amplified output beam relative to said optical interrogation beam.

24. The method of claim 21, wherein said effective coupling-mirror reflectivity is modified due to a change in the refractive index and/or optical absorption in the coating layer as the trace-gas is adsorbed in said oxide layer.

25. The method of claim 21, wherein said ROT further comprises a deformable mirror between said oxide layer and said reflective layer, the method further comprising altering the shape of said deformable mirror to tune said optical cavity.

26. The method of claim 25, comprising tuning said deformable mirror so that at least one Fabry Perot mode within said optical cavity is in resonance with said interrogation beam.

27. A method, comprising:
providing the resonant optical transducer (ROT) of claim 1;
operating said ROT at or above its laser threshold condition, wherein a intra-cavity beam is produced within said optical cavity and oscillates therein and wherein an output beam is coupled out of said optical cavity;
allowing a gas sample to flow into said intra-cavity gap, wherein said state selective oxide layer comprises oxide material selected to modify the effective coupling-mirror reflectivity of said reflective layer in the presence of a trace-species to be sensed; and
measuring changes in said beam to determine if said trace-species is present within said optical cavity.

28. The method of claim 27, wherein said changes are relative to said optical interrogation beam.

29. The method of claim 27, wherein said changes are selected from the group consisting of (i) changes in the properties of said oxide layer via non-resonant adsorption of a given species within said cavity and (ii) resonant photon interactions of said intra-cavity optical beam directly with a specific molecular absorption feature of a trace-gas specie.

30. The method of claim 27, wherein said effective coupling-mirror reflectivity is modified due to a change in the refractive index and/or optical absorption in the coating layer as the trace-gas is adsorbed in said oxide layer.

31. The method of claim 27, wherein said ROT further comprises a deformable mirror between said oxide layer and said reflective layer, the method further comprising altering the shape of said deformable mirror to tune said optical cavity.

32. The method of claim 31, comprising tuning said deformable mirror to provide at least one Fabry Perot mode in said optical cavity in resonance with said intra-cavity beam.

* * * * *